United States Patent [19]

Blohm et al.

[11] 4,317,817

[45] Mar. 2, 1982

[54] NOVEL STEROID 5α-REDUCTASE INHIBITORS

[75] Inventors: Thomas R. Blohm, Cincinnati; Brian W. Metcalf, Mason, both of Ohio

[73] Assignee: Richardson-Merrell Inc., Wilton, Conn.

[21] Appl. No.: 216,112

[22] Filed: Dec. 15, 1980

Related U.S. Application Data

[63] Continuation-in-part of Ser. No. 69,741, Aug. 27, 1979, abandoned, which is a continuation-in-part of Ser. No. 35,357, May 2, 1979, abandoned.

[51] Int. Cl.³ .................... A01N 47/08; A61K 31/655
[52] U.S. Cl. .................................. 424/226; 260/349; 260/397.5; 260/397.4; 260/239.55 C; 260/397.1; 260/239.55 R
[58] Field of Search ................. 260/349; 424/243, 226

[56] References Cited

U.S. PATENT DOCUMENTS 3,931,637  1/1976  Green et al. ......................... 260/349
4,011,315  3/1977  Marx et al. .......................... 260/349

OTHER PUBLICATIONS

The Journal of Clinical Investigation, vol. 49 (1970), pp. 1737-1745.
The Journal of Clinical Investigation, vol. 49 (1970), pp. 1746-1753.
The American Journal of Medicine, vol. 62 (1977), pp. 170-190.

*Primary Examiner*—Elbert L. Roberts
*Attorney, Agent, or Firm*—John J. Kolano; Raymond A. McDonald; William J. Stein

[57] ABSTRACT

Compounds of the following general formula are testosterone 5α-reductase inhibitors rendering the compounds useful in the treatment of acne and oily skin and benign prostatic hypertrophy:

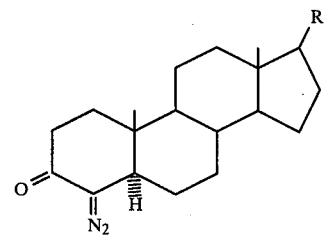

wherein R is:
=O, —OH, —OCO—alkyl $C_{1-5}$, —COOH, —CH$_2$OH, —COO—alkyl $C_{1-6}$, —COCH$_3$,

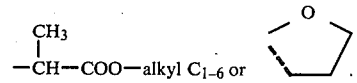

16 Claims, No Drawings

NOVEL STEROID 5α-REDUCTASE INHIBITORS

The present application is a continuation-in-part of copending U.S. application Ser. No. 69,741, filed Aug. 27, 1979 and that application is a continuation-in-part of U.S. application Ser. No. 35,357 filed May 2, 1979, now abandoned.

FIELD OF THE INVENTION

This invention relates to the use of certain steroid compounds for treatment of acne and oily skin, baldness and of prostate hypertrophy through inhibition of testosterone 5α-reductase.

BACKGROUND OF THE INVENTION

It is known that skin responds to androgens and is an active site of androgen metabolism. The androgen testosterone is metabolized in the skin to dihydrotestosterone (DHT) which is a more potent androgen than testosterone. As set out in Arch., Dermatol. 111, 1496 (1975) there is considerable evidence that DHT is involved in the pathogenesis of acne as well as other androgen associated conditions. Studies in the hamster flank organ, which is an androgen dependent sebaceous structure, indicate that DHT stimulates the growth of this structure. It has been found that acne-bearing skin produces from 2 to 20 times more DHT than normal skin. Therefore, it is believed that agents capable of blocking the formation of DHT would be effective in the treatment of an acne condition. Also, many studies indicate that prostatic hypertrophy may be treated by administering an agent that prevents the formation of DHT from testosterone, that is, a testosterone 5α-reductase inhibitor. Testosterone is converted to DHT by the enzymatic action of testosterone 5α-reductase. One possible means of blocking the formation of DHT is to inhibit the activity of testosterone 5α-reductase. More desirably, in the treatment of acne the activity of the 5α-reductase enzymes is inhibited locally, that is in the region of the acne-bearing skin.

Many workers in the art have believed that steroid compounds effective for testosterone 5α-reductase inhibition purposes required a $\Delta^4$-3-keto configuration and inferentially, at least presence of other ring A substituents would add little, and might even detract from the usefulness of a compound for inhibition purposes.

Thus, the numerous compounds discussed by Voigt and Hsia in their U.S. Pat. No. 3,917,829 and by Benson and Blohm in their U.S. Pat. No. 4,088,760 all contain the ring A $\Delta^4$-3-one structure.

It may be noted that the $\Delta^4$-3 keto steroids heretofore suggested for inhibition of the 5α-reductase act through competitive inhibition and their effectiveness depends upon maintaining a significant, perhaps substantial, concentration of inhibitor in the target organ, e.g., in the patient's skin or in the prostate. Manifestly competitive inhibitors offer a lesser degree of effectiveness than an irreversible or quasi-irreversible inhibitors.

A theory for irreversible inhibition of a 5α-reductase and $\Delta^5$-3-keto isomerase has been offered in U.S. Pat. No. 4,087,461, to which reference is made for details of the theory. Briefly the theory calls for employment of a steroid containing a potentially reactive group, which group becomes reactive when the target enzyme carries out its transformation. At that time a chemical reaction ensues, e.g., an alkylation, directly at the active site of the enzyme or so closely adjacent thereto as to irreversibly inhibit the enzyme. U.S. Pat. No. 4,087,461 suggests allenic seco-steroids for irreversible inhibition of $\Delta^5$-3-keto steroid isomerases and of testosterone 5α-reductase. U.S. Pat. No. 4,087,461 describes the enzyme catalyzed transformation as involving reaction at the C-4 position.

The present invention relates to use of certain 4-substituted steroids which inhibit the activity of 5α-reductase rendering said compounds useful in treating acne or oily skin. It is not known whether the inhibition is irreversible or is near to irreversible, i.e., quasi-irreversible, because the 4-substituted steroid does not readily decouple from the enzyme.

SUMMARY OF THE INVENTION

Compounds of the following formulas have been found to be at least quasi-irreversible inhibitors of the 5α-reductase.

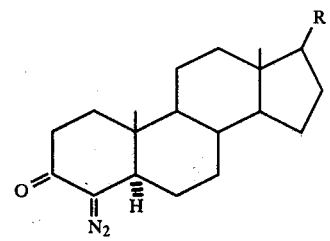

wherein R is:

=O, —OH, —OCO—alkyl $C_{1-5}$, —COOH, —CH$_2$OH,

—CHO, —COO—alkyl $C_{1-6}$, —COCH$_3$, —CH(CH$_3$)—CH$_2$OH,

—CH(CH$_3$)—CHO, —CH(CH$_3$)—COOH, —CH(CH$_3$)—COO—alkyl $C_{1-6}$ or

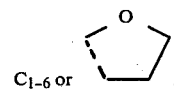

Thus, R can be monovalent or divalent. When R is monovalent, the substituent group involved has the β-configuration with respect to the steroid nucleus and a hydrogen satisfies the remaining valence at the 17-position of the steroid. When R is the divalent group

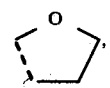

the oxygen is attached on the β-side of the steroid while the carbon is attached on the α-side. In addition, the R group can itself contain an asymmetric carbon atom, as in

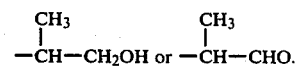

—CH(CH$_3$)—CH$_2$OH or —CH(CH$_3$)—CHO.

This asymmetric carbon is at the point of attachment of the group to the steroid which is the 20-position with respect to the steroid molecule. When the configuration at 20 is not specified, it can be either R or S; the present invention encompasses both of these isomers. Compounds having the R-configuration at the 20-position can also be designated as 20β-isomers or 20β-compounds.

A preferred set of compounds are those in which the R-substituent (the substituent at the 17-position of the steroid) is

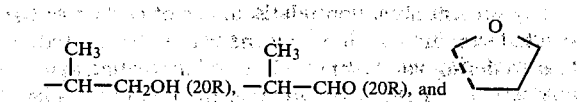
—CH—CH₂OH (20R), —CH—CHO (20R), and

It is believed that the inhibition attributable to the presence of the N₂ substituent at C-4 is cumulative of the competitive inhibition attributable to the presence of a preferred 17 substituent. By and large, the 17 substituents, i.e., R, are those described in the prior art, as for example by U.S. Pat. Nos. 3,917,829 and 4,088,760 for inhibition of the 5α-reductase.

As set forth hereinabove there is evidence that dihydrotestosterone (DHT) which is a metabolite of testosterone has a stimulatory effect on sebaceous glands and thereby is involved in the pathogenesis of acne, and agents which inhibit the formation of DHT would be useful in the treatment of acne. The compounds employed in the present invention have been found to be inhibitors of testosterone 5α-reductase, the enzyme which transforms testosterone to the more active androgen DHT. Hence, the compounds employed in the present invention, that is, the compounds of the formulas set out above, being inhibitors of testosterone 5α-reductase are useful in the treatment of acne and oily skin conditions. The compounds are also useful for treatment of benign prostatic hypertrophy and conditions such as male pattern baldness and DHT mediated hirsutism in females.

The potency of any enzyme inhibitor is often expressed in terms of its inhibition constant, Ki, which is defined mathematically in terms of established relationships of enzyme-catalyzed reaction rates to inhibitor and substrate concentrations. The derivation of these relationships and the mathematical definition of Ki are found in standard texts on enzymology. Simply stated, the Ki expresses quantitatively the combining power of the inhibitor for the enzyme; the lower the value of Ki, the greater the combining power (affinity). In the case of the substrate, the corresponding value is known as the Km, the relationship to combining power being roughly the same. The following comparison exhibits the increase in combining power for 5α-reductase obtained in the compounds of this series, over that of the substrate (testosterone) or one of the most potent previously known inhibitors.

|  | Ki |
|---|---|
| OH (testosterone structure) | $1.0 \times 10^{-6}$M (Km) |
| | testosterone |
| CH₂OH (structure) | $2.2 \times 10^{-7}$M |

-continued

|  | Ki |
|---|---|
| CH₂—OH (N₂ structure) | $3.5 \times 10^{-8}$M |

It can be seen that the representative compound of the present invention possesses 29 times the affinity of the substrate for the enzyme, and is 6.3 times as potent as the previous inhibitor.

The utility of the compounds employed in the present invention can be demonstrated by the ability of the compounds to inhibit the activity of 5α-reductase isolated from rat prostate gland. For example, using prostate microsomes containing testosterone 5α-reductase in an amount equivalent to 180 mg of fresh tissue, and 4—¹⁴C-testosterone at a concentration of $2 \times 10^{-6}$M, at $3 \times 10^{-8}$M (5α,20R) -4-diazo-21-hydroxy-20-methyl-pregnan-3-one was found to inhibit the conversion of testosterone to DHT and androstanediol (ADIOL) overall by 49%. Under the same conditions, a concentration of $3 \times 10^{-7}$M inhibited the conversion of testosterone to 5α-reduced products by 75%.

The effectiveness of the present compounds for the treatment of benign prostatic hypertrophy can be illustrated by the following procedure using 3 groups of castrated male rats. Starting 10 days after castration, Test Group I (5 animals) received 200 mg/kg of (5α,20R) -4-diazo-21-hydroxy-20-methylpregnan-3-one, given by gavage every 8 hours for 8 days as a suspension in 0.25 % aqueous Methocel. Starting 8 hours after the first dose of test compound, the animals also received testosterone daily at a dose of 0.6 mg/rat s.c. in olive oil. The last dose of test compound was administered 8 hours after the last dose of testosterone and the animals were sacrificed 8 hours later. Test Group II (12 animals) received only the testosterone treatment described above while the third group of rats (10 animals) served as controls and received the oral and s.c. vehicles only. At sacrifice, the ventral prostate was removed and weighed. The animals in Test Group I showed a significant reduction in prostatic weight as compared to Group II. In the same experiment, the weights of preputial glands of the rats treated with the inhibitor were significantly less than weights of preputial glands of the control rats. Preputial glands are sebaceous structures which exhibit the same androgen responsiveness as skin sebaceous glands, and this result therefore supports the utility of these compounds in the treatment of acne.

To achieve the desired anti-acne or anti-seborrheic effect the compounds employed in the present invention can be administered orally, parenterally, for example, intramuscularly and subcutaneously, and topically to a patient in need of treatment. Topical administration is preferred. As used herein in association with the treatment of acne or oily skin the term patient is taken to mean a warm-blooded mammal, for example, primates, human males and females having an acne condition or an oily skin condition in need of treatment. The compounds of the invention can be administered alone or suitably admixed in the form of a pharmaceutical preparation to the patient being treated. The amount of compound administered will vary with the severity of the acne condition or oily skin condition and repetitive treatment may be desired. For oral and parenteral administration the amount of compound administered, that is, the anti-acne or anti- seborrheic effective amount, is from 0.1 to 50 mg/kg of body weight per day and preferably from 1 to 30 mg/kg of body weight per day. Unit dosages for oral or parenteral administration may contain, for example, from 5 to 200 mg of the active ingredient. For topical administration the anti-acne or anti-seborrheic effective amount of the compounds of the invention on a percent basis can vary from 0.001% to 5% and preferably from 0.005% to 1%. For topical administration the formulated active ingredient, that is, a compound of the invention can be applied directly to the site requiring treatment or can be applied to the oral or nasal mucosa. Applicator sticks carrying the formulation may be employed in administering the compounds.

In the treatment of benign prostatic hypertrophy (bph) the compounds of the invention may be administered in various manners to the patient being treated to achieve the desired effect. As used herein in the treatment of bph the term patient is taken to mean male warm blooded animals, such as male rats, male dogs and human males. The compounds can be administered alone or in combination with one another. Also, the compounds can be administered in the form of a pharmaceutical preparation. The compounds may be administered orally, parenterally, for example, intravenously, intraperitoneally, intramuscularly or subcutaneously, including injection of the active ingredient directly into the prostate. Slow release implants can also be used. The amount of compound administered will vary over a wide range and can be any effective amount. Depending on the patient to be treated, the condition being treated and the mode of administration, the effective amount of compound administered will vary from about 0.1 to 50 mg/kg of body weight per day and preferably from 1 to 30 mg/kg of body weight per day. Unit dosages for oral or parenteral administration may contain, for example, from 5 to 200 mg of a compound of the invention.

These dosage ranges represent the amount of compound that will be effective in reducing the size of the prostate, i.e., the amount of compound effective in treating bph. The compounds can be administered from onset of hypertrophy of the prostate to regression of the symptoms, and may be used as a preventive measure.

Topical formulation can be, for example, in the form of a solution, suspension, emulsion, gel or cream of either the oil-in-water or water-in-oil type, ointment, paste, jelly, paint or powder. Suitable bases for the topical preparation may be of any conventional type such as oleaginous bases, for example, olive oil, cottonseed oil, petrolatum, white petrolatum, mineral oils, silicones, such as, dimethylpolysiloxane, or methylphenylpolysiloxane, lanolines, polyethyleneglycol, glyceryl monostearate, methylcellulose and hydroxymethylcellulose. The topical formuation may contain pharmaceutically acceptable surfactants, wetting agents, dispersing agents, emulsifiers, penetrants, emollients, detergents, hardeners, preservatives, fillers, antioxidants, perfumes, cooling agents, such as, menthol, soothing agents, such as, camphor, or coloring agents, such as, zinc oxide. Aerosol preparations of a solution, suspension or emulsion containing the active ingredient in the form of a finely ground powder can also be employed for topical administration. The aerosol may be packaged in a pressurized aerosol container together with a gaseous or liquified propellant, for example, dichlorodifluoromethane, dichlorodifluoromethane with dichlorodifluoroethane, carbon dioxide, nitrogen or propane with the usual adjuvant such as cosolvent and wetting agents as may be necessary or desirable. The compounds may also be administered in a non-pressurized form such as in a nebulizer or atomizer.

Following are illustrative topical pharmaceutical formulations which may be employed in practicing the present invention:

| SOLUTION | |
|---|---|
| (5α,20R)-4-diazo-21-hydroxy-20-methyl pregnan-3-one | 0.85 g |
| Alcohol | 78.9 ml |
| Isopropyl myristate | 5.0 g |
| Polyethylene glycol 400 | 10.0 g |
| Purified water qs ad | 100 ml |

Combine the alcohol, isopropyl myristate and polyethylene glycol 400 and dissolve the drug substance therein. Add sufficient purified water to give 100 ml.

| A GEL | | |
|---|---|---|
| (a) | (5α,20R)-4-diazo-21-hydroxy-20-methylpregnan-3-one | 0.85 g |
| (b) | Alcohol | 78.9 ml |
| (c) | Isopropyl myristate | 5.0 g |
| (d) | Polyethylene glycol 400 | 10.0 g |
| (e) | Carbopol 940 (Carboxypolymethylene) | .75 g |
| (f) | Triethylamine | qs |
| (g) | Purified water qs ad | 85 g |

Disperse the Carbopol 940 in the isopropyl myristate. To 38 ml of alcohol add 7 ml of purified water and the polyethylene glycol 400 and mix. Combine the two phases and mix until well dispersed. Add sufficient triethylamine to give a neutral pH. Dissolve the drug substance in the balance of the alcohol and mix well into the batch. Add and mix sufficient purified water to provide 85 g of finished product.

| APPLICATOR STICK | | |
|---|---|---|
| (a) | (5α,20R)-4-diazo-21-hydroxy-20-methylpregnan-3-one | 0.85 g |
| (b) | Absolute alcohol | 75 ml |
| (c) | Polyethylene glycol 400 | 10.0 g |
| (d) | Isopropyl myristate | 5.0 g |
| (e) | Stearic acid | 4.3 g |
| (f) | Sodium hydroxide | 0.55 g |
| (g) | Purified water qs ad | 85 g |

Combine the absolute alcohol, polyethylene glycol 400 and isopropyl myristate. Add the stearic acid and heat the mixture to about 65° C. Dissolve the sodium hydroxide in a small amount of water, add and mix. Add sufficient water to provide 85 g of finished product. After formation of the applicator stick base, the drug substance is suspended therein immediately before depositing and solidifying the formulation.

| AEROSOL FOAM | | |
|---|---|---|
| (a) | (5α,20R)-4-diazo-21-hydroxy-20-methylpregnan-3-one | 1.0 g |

| AEROSOL FOAM | |
|---|---|
| (b) Propylene glycol | 96.0 g |
| (c) Emulsifying Wax NF XIV | 3.0 g |
| (d) Dichlorodifluoromethane:cryofluorane (20:80) | 6.9 g |

Dissolve the drug substance in the propylene glycol. Add the emulsifying wax and heat to approximately 70° C. Stir while cooling to room temperature. Charge a suitable aerosol unit with this concentrate and 6.9 g of dichlorodifluoromethane:cryofluorane (20:80).

| TOPICAL CREAM, VANISHING o/w | |
|---|---|
| (a) (5α,20R)-4-diazo-21-hydroxy-20-methylpregnan-3-one | 1 g |
| (b) Stearyl alcohol | 15 g |
| (c) Sorbitan Monostearate | 2 g |
| (d) Polyoxyethylene Sorbitan Monostearate | 2.3 g |
| (e) Propylene glycol | 5 g |
| (f) Methylparaben | 0.025% |
| (g) Propylparaben | 0.015% |
| (h) Purified Water | qs |

| POWDER | |
|---|---|
| (a) (5α,20R)-4-diazo-21-hydroxy-20-methylpregnan-3-one | 1 g |
| (b) Silicon dioxide, anhydrous | 0.5 g |
| (c) Cornstarch, lactose, fine powder | qs |

| OLEAGINOUS OINTMENT | |
|---|---|
| (a) (5α,20R)-4-diazo-21-hydroxy-20-methylpregnan-3-one | 1 g |
| (b) White wax | 5 g |
| (c) White petrolatum qs | 100 g |

| ABSORPTION OINTMENT BASE | |
|---|---|
| (a) (5α,20R)-4-diazo-21-hydroxy-20-methylpregnan-3-one | 1 g |
| (b) Cholesterol | 3 g |
| (c) Stearyl alcohol | 3 g |
| (d) White wax | 8 g |
| (e) White petrolatum qs | 100 g |

| WATER SOLUBLE OINTMENT DOSE | |
|---|---|
| (a) (5α,20R)-4-diazo-21-hydroxy-20-methylpregnan-3-one | 1 g |
| (b) Polyethylene glycol 400 | 40 g |
| (c) Polyethylene glycol 0 qs | 100 g |

| PASTE | |
|---|---|
| (a) (5α,20R)-4-diazo-21-hydroxy-20-methylpregnan-3-one | 1 g |
| (b) Starch | 25 g |
| (c) Zinc oxide | 25 g |
| (d) White petrolatum qs | 100 g |

| AEROSOL FOAM | |
|---|---|
| (a) (5α,20R)-4-diazo-21-hydroxy-20-methylpregnan-3-one | 1 g |
| (b) Emulsifying wax | 3 g |
| (c) Stearyl alcohol | 2 g |
| (d) Diglycol stearate | 2 g |
| (e) Propylene glycol | 92 g |

The compounds in treating acne and an oily skin condition may be used in combination with other anti-acne preparations, antiseptics, antiinfective agents, keratolytic agents, for example, resorcinol, comedolytic agents, or agents having a retinoic acid-like action, corticoids or other antiinflammatory agents, thioglycolates, ethyl lactate or benzoyl peroxide. The following formulations are illustrative of pharmaceutical preparations for topical application comprising a compound in combination with a keratolytic agent.

| AEROSOL FOAM | |
|---|---|
| (a) (5α,20R)-4-diazo-21-hydroxy-20-methylpregnan-3-one | 1 g |
| (b) Resorcinol monoacetate | 1 g |
| (c) Emulsifying wax NF | 3 g |
| (d) Stearyl alcohol | 2 g |
| (e) Diglycol stearate | 2 g |
| (f) Propylene glycol | 91 g |

Dissolve the drug substance in the propylene glycol. Add the emulsifying wax and heat to about 70° C. Stir while cooling to room temperature. Charge a suitable aerosol unit with the concentrate and 6.9 g of dichlorodifluoromethane:cryofluorane (20:80).

| A GEL | |
|---|---|
| (a) (5α,20R)-4-diazo-21-hydroxy-20-methylpregnan-3-one | 0.85 g |
| (b) Resorcinol | 0.85 g |
| (c) Alcohol | 78.9 ml |
| (d) Isopropyl myristate | 5.0 g |
| (e) Polyethylene glycol 400 | 10.0 g |
| (f) Carbopol 940 (carboxypolymethylene) | 0.75 g |
| (g) Triethylamine | qs |
| (h) Purified water qs ad | 85 g |

Disperse the Carbopol 940 in the isopropyl myristate. To 38 ml of alcohol add 7 ml of purified water and the polyethylene glycol 400 and mix. Combine the two phases and mix until well dispersed. Add sufficient triethylamine to give a neutral pH. Dissolve the drug substance and the resorcinol in the balance of the alcohol and mix well into the batch. Add and mix sufficient purified water to provide 85 g of finished product.

For oral administration the compounds can be formulated into solid or liquid preparations, such as, capsules, pills, tablets, troches, powders, solutions, suspensions, or emulsions. The compounds can be applied in the form of an aerosol containing finely divided particles of the active ingredient or a solution, suspension or emulsion of the active ingredient. The solid unit dosage forms can be a capsule which can be of the ordinary gelatin type containing the active compound and a carrier, for example, lubricants and inert fillers such as lactose, sucrose and corn starch. In another embodiment, an active compound of the invention can be tableted with conventional tablet bases such as lactose, sucrose and corn starch in combination with binders such as acacia, corn starch or gelatin, disintegrating agents such as potato starch or alginic acids and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water-in-oil with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanols and glycols, such as, propylene glycol or polyethylene glycol are preferred liquid carriers, particularly for injectable solutions.

The compounds can be administered in the form of a depot injection or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones, for examples, Silastic, silicone rubber manufactured by the Dow-Corning Corporation.

The following are illustrative pharmaceutical formulations suitable for oral or parenteral administration which may be employed in practicing the present invention:

| TABLET | |
|---|---|
| (a) (5α,20R)-4-diazo-21-hydroxy-20-methylpregnan-3-one | 75 g |
| (b) Lactose | 1.216 Kg |
| (c) Corn starch | 0.3 Kg |
| Mix the active ingredient, the lactose and corn starch uniformly. Granulate with 10% starch paste. Dry to a moisture content of about 2.5%. Screen through a No. 12 mesh screen. Add and mix the following: | |
| (a) Magnesium stearate | 0.015 Kg |
| (b) Corn starch qs ad | 1.725 Kg |

Compress on a suitable tablet machine to a weight of 0.115 g/tablet.

| SOFT GELATIN CAPSULE | |
|---|---|
| (a) (5α,20R)-4-diazo-21-hydroxy-20-methylpregnan-3-one | 0.25 Kg |
| (b) Polysorbate 80 | 0.25 Kg |
| (c) Corn oil qs ad | 25.0 Kg |

Mix and fill into 50,000 soft gelatin capsules.

| IM DEPOT INJECTION | |
|---|---|
| (a) (5α,20R)-4-diazo-21-hydroxy-20-methylpregnan-3-one | 5.0 mg |
| (b) Anhydrous chlorobutanol | 5.0 mg |
| (c) Aluminum monostearate | 50.0 mg |
| (d) Peanut oil qs ad | 1.0 ml |

Dissolve or disperse the ingredients in the peanut oil.

| DEPOT-IMPLANT | |
|---|---|
| (a) (5α,20R)-4-diazo-21-hydroxy-20-methylpregnan-3-one | 5 mg |
| (b) Dimethylsiloxane | 240 mg |
| (c) Catalyst qs | |

Disperse the drug substance in the fluid dimethylsiloxane. Add the catalyst and cast into a suitable monolytic structure.

Alternatively, the drug substance may be enclosed by a precast, polydimethylsiloxane envelope.

Alternatively, the drug substance may be dispersed in a suitable amount of hydroxyethyl acrylate subsequently polymerized and cross-linked by the addition of ethylenedimethylacrylate, and an oxidizing agent, to yield a 3-dimensional ethylene glycomethacrylate moldable gel (Hydron).

| IM INJECTIONS | |
|---|---|
| A. Oil Type: | |
| (a) (5α,20R)-4-diazo-21-hydroxy-20-methylpregnan-3-one | 25 mg |
| (b) BHA, BHT aa | 0.01% w/v |

| -continued | |
|---|---|
| (c) Peanut oil or sesame oil qs | 1.0 ml |
| B. Suspension Type: | |
| (a) (5α,20R)-4-diazo-21-hydroxy-20-methylpregnan-3-one | 25 mg |
| (b) Sodium carboxymethylcellulose | 0.5% w/v |
| (c) Sodium bisulfite | 0.02% w/v |
| (d) Water for injection, qs | 1.0 ml |
| BUCCAL OR SUBLINGUAL TABLET | |
| (a) (5α,20R)-4-diazo-21-hydroxy-20-methylpregnan-3-one | 1% |
| (b) Calcium stearate | 1% |
| (c) Calcium saccharin | 0.02% |
| (d) Granular mannitol | qs |

Mix and compress on a suitable table machine to a weight of 0.115 g/tablet.

The compounds herein described can be prepared from the Δ⁴-3 keto precursor

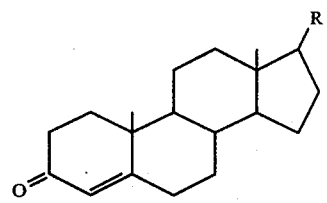

wherein R is as already described, but may be blocked, e.g., forming a siloxy ether or a ketal as appropriate and desirable during the reaction sequence. For instance the reaction sequence set out below, and followed in Example 1 employs a di-methyl tertiary butyl siloxy ether blocking group on the 17-substituent to protect the 17substituent during the reaction sequence used to add a 4-benzoyl group. Then R may be unblocked and after the diazo transfer is carried out, transformed to the ultimate substituent, e.g., oxidized to an aldehyde.

When R contains an alcohol, the starting material will be the alcohol itself. If R contains an aldehyde, the corresponding alcohol is utilized as the starting material, and later the alcohol group is transformed into the aldehyde.

The alcohol function is protected through forming the dimethyl-t-butyl silyl ether by the technique described by E. J. Corey et al., J. Am. Chem. Soc. 94, 6190 (1972).

When R=COCH₃ (i.e., the staring material is progesterone) the side chain is protected by first forming the ketal

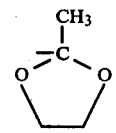

The (protected) 3-keto Δ⁴ steroid, e.g., Compound A of the reaction sequence flow sheet which follows, is subjected to dissolving metal reduction using Li in NH₃ in aniline or tert-butyl alcohol for the proton donor at −78° to −33° C. for 1 to 60 minutes as generally described by G. Stork et al., J. Am. Chem. Soc. 96, 7114 (1974). Then the enolate ion is trapped with trimethylsilyl chloride and the resulting enol ether, e.g., Compound B, isolated.

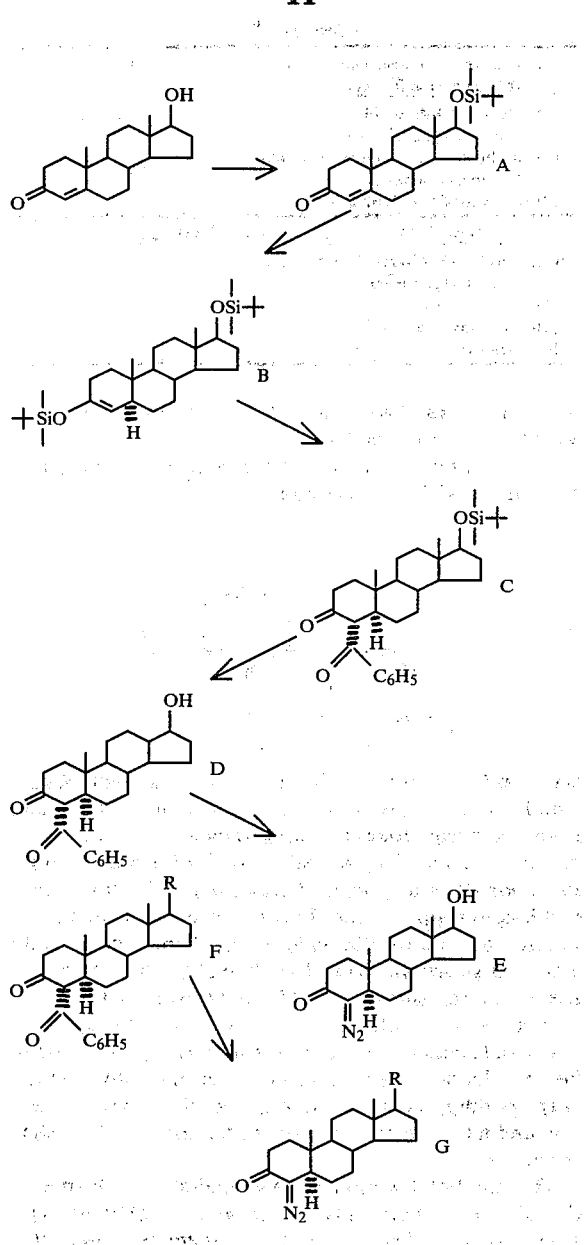

The enolate anion is then regenerated from the enol ether using alkyl lithiums, e.g., methyl or butyl lithium in ethers, such as, tetrahydrofuran or diethyl ether at 0°-25° C. for 1 to 60 minutes, and is reacted with benzoyl chloride, or a lower alkyl $C_{1-4}$ acid chloride for 1 to 20 minutes at −100° to −70° C. in, e.g., diethyl ether or tetrahydrofuran (Compound C).

Thereafter the alcohol function is unblocked with F$\theta$ or acid as described by E. J. Corey et al., J. Am. Chem. Soc. 94, 6190 (1972) or else by reaction with a tetrafluoroborate salt such as the lithium, sodium, zinc, tin, magnesium, silver, potassium, triphenylcarbenium, trialkyloxonium (e.g., methyl, ethyl, propyl, butyl) tetrafluoroborate in aprotic solvents, acetonitrile, dimethylformamide, dimethylacetamide, ethers, methylene chloride, chloroform or combinations thereof at temperatures of from about 0°-100° C. for 1 to 72 hours. The procedure will effect cleavage of the tert-butyldimethylsilyl ether to the corresponding alcohols, both primary and secondary (Compound D).

When R=OH, CH$_2$OH or

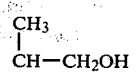

or other alcohols as defined by R the diazo transfer reaction (to Compound E) may follow directly, by treatment of equivalent amount of Compound D, and trialkylamines, such as, triethylamine, with sodium hydride to generate the enolate, then p-toluene-sulfonyl azide is added to introduce the diazo function as described by J. B. Hendrickson et al., J. Org. Chem. 33, 3610 (1968), usually performed in ether or tetrahydrofuran at 0°-25° C., 1 to 24 hours.

When R is other than

or one of the alcohol containing groups conversion at the 17-position to the desired 17-substituent can be carried out after the diazo transfer reaction.

The alcohol group may be oxidized to the aldehyde or ketone by standard procedures, for example, using pyridinium chlorochromate as described by E. J. Corey et al., Tet. Ltrs., 2647 (1975), or using chromium trioxide/pyridine (R. W. Ratcliffe, Org. Syn., 1973) or to the acid using Jones Reagent (R. Bowden et al., J. Chem. Soc., 39, (1966).

When R is OCO-alkyl these are obtained from the alcohol by reaction with a $C_{1-6}$ alkyl acid chloride or anhydride in pyridine as solvent (0°-25° C., 1 to 24 hours).

In the instance wherein R=—COCH$_3$ the actual starting material for the reaction sequence is the 20-ketal, the ketal protecting group being removed prior to the diazo transfer reaction by exchange in acetone or propanone using p-toluenesulfonic acid as the catalyst at 25°-60° C. for 1 to 24 hours.

The furan

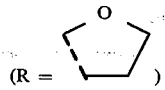

may be utilized directly without need for any blocking groups and the reaction sequence proceeds directly from the starting compound to the ultimate diazo compound.

The following examples describe preparation of the 4-diazo compounds of this invention.

EXAMPLE 1

Testosterone dimethyl t-butylsilylether (Compound A)

A mixture of testosterone (1.0 g, 3.5 mmole), t-butyldimethylsilyl chloride (627 mg, 4.2 mmole) and imidazole (287 mg, 4.2 mmole) in dimethylformamide (4 ml) is stirred overnight at 40° C. The mixture is then poured into ice water and the resulting precipitate filtered off and recrystallized from methanol to afford 1.35 g.

3-Trimethylsiloxy-17β-(dimethyl-t-butylsiloxy)-5α-andost-3-ene (Compound B)

Testosterone dimethyl-t-butylsilyl ether (12.0 g, 29.8 mmole) in tetrahydrofuran (70 ml) is added to ammonia containing aniline (2.7 g, 29.8 mmole) and lithium (625 mg, 89 mmole). After 1 hour the blue solution is treated dropwise with isoprene until the blue color is dissipated. The ammonia is allowed to evaporate and the residue dried under vacuum (0.5 mm). Tetrahydrofuran (50 ml) is then added, the solution cooled to 0° C., and treated with a solution of trimethylsilyl chloride (12 ml) and triethylamine (12 ml) which had previously been centrifuged. After 15 minutes the mixture is diluted with pentane and washed with chilled 0.5 M HCl, then chilled aqueous sodium bicarbonate, then dried (MGSO$_4$) and concentrated. The residue is crystallized from ethyl acetate to afford 6.6 g. (The mother liquors are chromatographed on silica gel. Elution with 10% ether-pentane affords a fraction which is recrystallized from ethyl acetate (2.2 g).) M.P. 126° C.

4-Benzoyl-17β-(dimethyl-t-butylsiloxy)-5α-andostan-3-one (Compound C)

To the enol ether (4.89 g, 10.27 mmole) in ether (20 ml) is added methyl lithium (5.5 ml of a 2.05 M solution, 11.3 mmole). After 1 hour at 25° C. the solution is taken up in a syringe and added slowly to a solution of benzoyl chloride (1.45 g, 10.3 mmole) in ether (30 ml) at −70° C. After 5 minutes aqueous ammonium chloride is added and the products isolated by ether extraction. The residue, after evaporation of the ether, is recrystallized from carbon tetrachloride to afford 2.0 g.

4-Benzoyl-17β-hydroxy-5α-andostan-3-one (Compound D)

The silyl ether (1.64 g, 3.2 mmole) in dichloromethane (50 ml) is treated with tritylfluoroborate (1.27 g, 3.84 mmole) for 1 hour at 25° C. This solution is then washed with aqueous ammonium chloride, dried and evaporated. The residue is chromatographed on silica gel. Elution with 1% methanol-chloroform afforded a fraction which is recrystallized from ethyl acetate-pentane (1.0 g).

4-Diazo-17β-hydroxy-5α-androstan-3-one (Compound E)

The diketone (3.5 mg, 0.8 mmole) in tetrahydrofuran (2.0 ml) is added to sodium hydride (48 mg, of a 50% dispersion) in tetrahydrofuran (5 ml). After 30 minutes, tosylazide (157 mg, 0.8 mmoles) in tetrahydrofuran is added and the mixture stirred overnight at 25° C. Ether is then added, the mixture filtered, then washed with water, dried and evaporated. The residue is chromatographed, the fraction eluted with 70% ether-petrol being collected. Recrystallization from chloroform-hexane afforded yellow crystals (26 mg), m.p. 171° C.

EXAMPLE 2

4-Benzoyl-5α-androstane-3,17-dione

4-Benzoyl-17β-hydroxy-5α-androstan-3-one made as in Example 1 (788 mg, 2 mmole) in 2 ml of CH$_2$Cl$_2$ is added to pyridinium chlorochromate (650 mg, 3 mmole) suspended in CH$_2$Cl$_2$ (2 ml) at 25° C. After 2 hours, ether is added and the solvent decanted. This is then filtered through Florisil, the eluate evaporated and the residue recrystallized from chloroform-heptane.

4-Diazo-5α-androstane-3,17-dione

The triketone (350 mg, 0.8 mmole) in tetrahydrofuran (2.0 ml) is added to sodium hydride (48 mg, of a 50% dispersion) in tetrahydrofuran (5 ml). After 30 minutes, tosylazide (157 mg, 0.8 mmole) in tetrahydrofuran is added and the mixture stirred overnight at 25° C. Ether is then added, the mixture filtered, then washed with water, dried and evaporated. The residue is chromatographed, the fraction eluted with 70% ether-petrol being collected. Recrystallization from chloroform-hexane afforded yellow crystals (35 mg).

EXAMPLE 3

The series of reactions described in this example employ the following sequence of compounds:

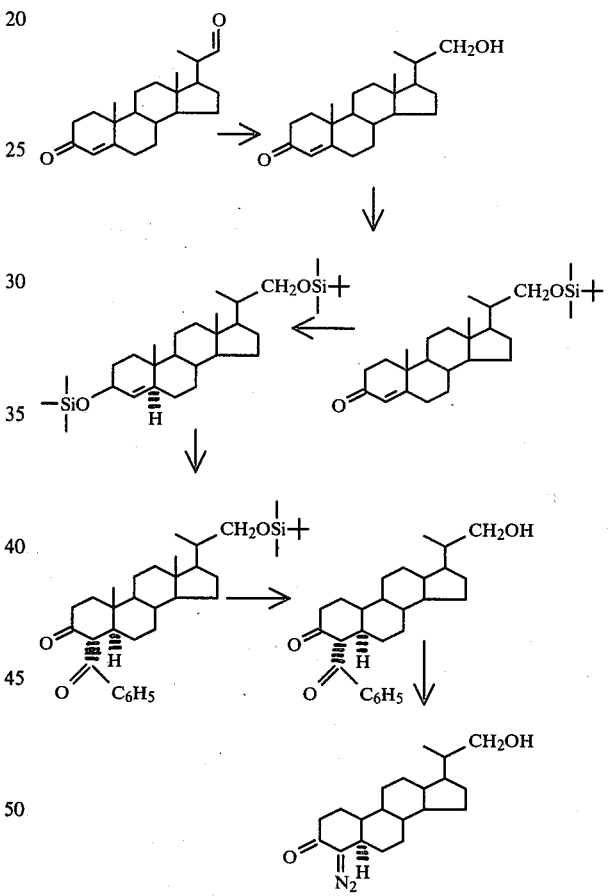

(20R)-21-Hydroxy-20-methylpren-4-en-3-one

To (20R)-3-oxopregn-4-ene-20-carboxaldehyde (16.4 g, 50 mmole) in ethanol (250 ml) and THF (50 ml) at 0° C. is added a solution of NaBH$_4$ (675 mg, 12.5 mmole) in ethanol (125 ml) dropwise. The mixture is stirred at 25° C. overnight, then neutralized by the addition of glacial acetic acid, then concentrated on the rotary evaporator. The residue is taken up in chloroform and washed with saturated aqueous NaHCO$_3$, then brine, then dried and concentrated. The residue is recrystallized from chloroformpentane to afford the alcohol as a colorless solid (12.6 g, 77%). M.P. 132.5° C.

(20R)-21-(Dimethyl-t-butylsiloxy)-20-methylpregn-4-en-3-one

A mixture of (20R)-21-hydroxy-20-methylpregn-4-en-3-one, t-butyldimethylsilyl chloride (10 g, 30.3 mmole) and imidazole in dimethylformamide (50 ml) is stirred overnight at 40° C. The mixture is then poured into ice water and the resulting precipitate filtered off and recrystallized from methanol to afford 8.6 g of the 21-ether.

(5α,20R)-3-Trimethylsiloxy-21-(dimethyl-t-butylsiloxy)-20-methylpregn-3-ene (20R)-21-(Dimethyl-t-butylsiloxy)-20methylpregn-4-en-3-one (2.0 g, 4.5 mmole) in tetrahydrofuran (20 ml is added to ammonia containing aniline (420 mg, 4.5 mmole) and lithium (100 mg, 15 mmole). After 1 hour the blue solution is treated dropwise with isoprene until the blue color is dissipated. The ammonia is allowed to evaporate and the residue dried under vacuum (0.5 mm). Tetrahydrofuran (20 ml) is then added, the solution cooled to 0° C., and treated with a solution of trimethylsilyl chloride (4 ml) and triethylamine (4 ml) which had previously been centrifuged. After 15 minutes the mixture is diluted with pentane and washed with chilled 0.5 M HCl, then chilled aqueous sodium bicarbonate, then dried (MgSO$_4$) and concentrated. The residue is crystallized from ethyl acetate to afford 1.6 g of the enol ether. M.P. 113° C.

(5α,20R)-4-Benzoyl-21-(dimethyl-t-butylsiloxy)-20-methyl-pregnan-3-one

To the enol ether (5α,20R)-3-trimethylsiloxy-21-(dimethyl-t-butylsiloxy)-20-methylpregn-3-ene (5.08 g, 9.8 mmole) in ether (20 ml) is added methyl lithium (5.5 ml of a 2.05 M solution, 11.3 mmole). After 1 hour at 25° C. the solution is taken up in a syringe and added slowly to a solution of benzoyl chloride (1.54 g, 1.27 mmole) in ether (30 ml) at −70° C. After 5 minutes aqueous ammonium chloride is added and the products isolated by ether extraction. The residue, after evaporation of the ether, is recrystallized from chloroform-heptane to afford 450 mg of the 4-benzoyl compound. M.P. 169° C.

(5α,20R)-4-Benzoyl-21-hydroxy-20-methylpregnan-3-one

The silyl ether (5α,20R)-4-benzoyl-21-(dimethyl-t-butylsiloxy)-20-methylpregnan-3-one (1.06 g, 2.0 mmole in dichloromethane (50 ml) is treated with tritylfluoroborate (660 mg, 2 mmole) for 1 hour at 25° C. This solution is then washed with aqueous ammonium choride, dried and evaporated. The residue is chromatographed on silica gel. Elution with 1% methanol-chloroform affords a fraction which is recrystallized from ethyl acetate-pentane (500 mg). M.P. 236°–238° C.

(5α,20R)-4-Diazo-21-hydroxy-20-methylpregnan-3-one

The (5α,20R)-4-benzoyl-21-hydroxy-20-methylpregnan-3-one (436 mg, 1.0 mmole) in tetrahydrofuran (2.0 ml) is added to sodium hydride (48 mg, of a 50% dispersion) in tetrahydrofuran (5 ml). After 30 minutes, tosylazide (196 mg, 1.0 mmole) in tetrahydrofuran is added and the mixture stirred overnight at 25° C. Ether is then added, the mixture filtered, then washed with water, dried and evaporated. The residue is chromatographed on silica gel, the fraction eluted with 70% ether-petrol being collected. Recrystallization from chloroform-hexane affords yellow crystals (30 mg), m.p. (210° de- comp.), of (5α20R)-4-diazo-21-hydroxy-20-methylpregnan-3-one.

If the above procedure is repeated starting with (20S)-21-hydroxy-20-methylpregn-4-en-3-one, the corresponding (20S)-compounds are obtained.

EXAMPLE 4

(5α,20R)-4-Diazo-3-oxopregnane-20-carboxaldehyde

To 60 mg of (5α,20R)-4-diazo-21-hydroxy-20-methyl-pregnane-3-one in 5 ml of dichloromethane is added 60 mg of pyridinium chlorochromate and the mixture is stirred for 16 hours at room temperature. It is then diluted with ether and filtered through a small column of silica gel in ether. Evaporation of the solvent leaves a solid which is recrystallized from ether to give (5α,20R)-4-diazo-3-oxopregnane-20-carboxaldehyde which melts with decomposition.

EXAMPLE 5

The series of reactions described in this example employ the following sequence of compounds:

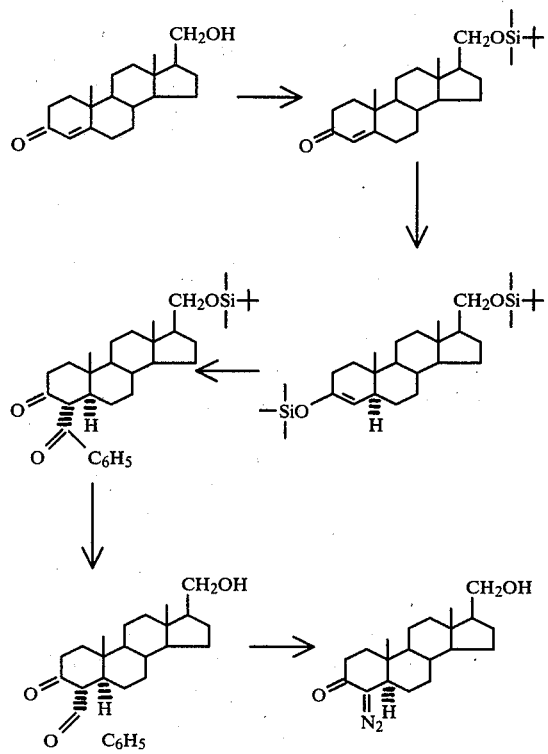

17β-(Dimethyl-t-butylsiloxymethyl)androst-4-en-3-one

A mixture of 17β-hydroxymethylandrost-4-en-3-one (1.0 g, 3.5 mmole), t-butyldimethylsilyl chloride (627 mg, 4.2 mmole) and imidazole (287 mg, 4.2 mmole) in dimethylformamide (4 ml) is stirred overnight at 40° C. The mixture is then poured into ice water and the resulting precipitate filtered off and recrystallized from methanol to afford 1.35 g of the desired product.

3-Trimethylsiloxy-17β-(dimethyl-t-butylsiloxymethyl)-5α-androst-3-ene

17β-(Dimethyl-t-butylsiloxymethyl)androst-4-en-3one (12.0 g, 29.8 mmole) in tetrahydrofuran (70 ml) is added to ammonia containing aniline (2.7 g, 29.8 mmole) and lithium (625 m, 89 mmole). After 1 hour the blue solution is treated dropwise with isoprene until the blue color dissipates. The ammonia is allowed to evaporate and the residue dried under vaccum (0.5 mm). Tetrahydrofuran (50 ml) is then added, the solution cooled to 0° C., and treated with a solution of trimethylsilyl chloride (12 ml) and triethylamine (12 ml) which had previously been centrifuged. After 15 minutes the mixture is diluted with pentane and washed with chilled 0.5 M HCl, then chilled aqueous sodium bicarbonate, then dried (MgSO$_4$) and concentrated. The residue is crystallized from ethyl acetate to afford the desired enol ether (6.6 g). The mother liquors are chromatographed on silica gel. Elution with 10% ether-pentane affords a fraction which is recrystallized from ethyl acetate (2.4 g).

4-Benzoyl-17β-(dimethyl-t-butylsiloxymethyl)-5α-androstan-3-one

To the enol ether (4.89 g, 10.27 mmole) in ether (20 ml) is added methyl lithium (5.5 ml of a 2.05 M solution, 11.3 mmole). After 1 hour at 25° C. the solution is taken up in a syringe and added slowly to a solution of benzoyl chloride (1.45 g, 10.3 mmole) in ether (30 ml) at 70° C. After 5 minutes aqueous ammonium chloride is added and the products isolated by ether extraction. The residue, after evaporation of the ether, is recrystallized from carbon tetrachloride to afford 2.2 g of the 4-benzoyl ether.

4-Benzoyl-17β-hydroxymethyl-5α-androstan-3-one

The silyl ether (1.64 g, 3.2 mmole) in dichloromethane (50 ml) is treated with tritylfluoroborate (1.27 g, 3.84 mmole) for 1 hour at 25° C. This solution is then washed with aqueous ammonium chloride, dried and evaporated. The residue is chromatographed on silica gel. Elution with 1% methanol-chloroform affords a fraction which is recrystallized from ethyl acetate-pentane to give the 4-benzoyl compound (800 mg).

4-Diazo-17β-hydroxymethyl-5α-androstan-3-one

The 4-benzoyl compound (350 mg, 0.8 mmole) in tetrahydrofuran (2.0 ml) is added to sodium hydride (48 mg, of a 50% dispersion) in tetrahydrofuran (5 ml). After 30 minutes, tosylazide (157 mg, 0.8 mmole) in tetrahydrofuran is added and the mixture stirred overnight at 25° C. Ether is then added, the mixture filtered, then washed with water, dried and evaporated. The residue is chromatographed, the fraction eluted with 70% ether-petrol being collected. Recrystallization from chloroform-hexane affords yellow crystals (30 mg) of the desired product.

EXAMPLE 6

4-Diazo-17β-hydroxymethyl-5αandrostan-3-one is oxidized with pyridinium chlorochromate according to the procedure described in Example 4 to give 4-diazo-3-oxo-5α-androstane-17β-carboxaldehyde. In a similar manner, 4-diazo-17β-hydroxy-5α-androstan-3-one is oxidized with pyridinium chlorochromate to give 4-diazo-5α-androstane-3,17-dione.

EXAMPLE 7

One g of 4-benzoyl-17β-hydroxy-5α-androstan-3-one prepared as in Example 1 in pyridine (5ml) and acetic anhydride (5ml) is maintained at 25° C. for 10 hours, then diluted with ether. The ether solution is washed with 1 N HCl, saturated NaHCO$_3$, then dried, evaporated and the residue crystallized from ethyl acetate to afford the 17-acetate.

4-Diazo-17β-acetoxy-5α-androstan-3-one

The triketone (350 mg, 0.8 mmole) in tetrahydrofuran (2.0 ml) is added to sodium hydride (48 mg, of a 50% dispersion) in tetrahydrofuran (5 ml). After 30 minutes, tosylazide (157 mg, 0.8 mmole) in tetrahydrofuran is added and the mixture stirred overnight at 25° C. Ether is then added, the mixture filtered, then washed with water, dried and evaporated. The residue is chromatographed, the fraction eluted with 70% ether-petrol being collected. Recrystallization from chloroform-hexane affords yellow crystals (30 mg).

EXAMPLE 8

Use of progesterone (20-ethylenedioxy ketal) to prepare the corresponding 4-diazo compound is described in the present example.

3-Trimethylsiloxy-20-ethylenedioxy-5α-pregn-3-ene

Progesterone 20-ethylenedioxy ketal (10.7 g, 30 mmole) in tetrahydrofuran (70 ml) is added to ammonia containing aniline (2.7 g, 30 mmole) and lithium (625 mg, 89 mmole). After 1 hour the blue solution is treated dropwise with isoprene until the blue color dissipates. The ammonia is allowed to evaporate and the residue dried under vacuum (0.5 mm). Tetrahydrofuran (50 ml) is then added, the solution cooled to 0° C., and treated with a solution of trimethylsilyl chloride (12 ml) and triethylamine (12 ml) which had previously been centrifuged. After 15 minutes the mixture is diluted with pentane and washed with chilled 0.5 M HCl, then chilled aqueous sodium bicarbonate, then dried (MgSO$_4$) and concentrated. The residue is crystallized from ethyl acetate to afford 6.0 g of the desired enol ether.

4-Benzoyl-20-ethylenedioxy-5α-pregnan-3-one

To the enol ether (4.4 g, 10.27 mmole) in ether (20 ml) is added methyl lithium (5.5 ml of a 2.05 M solution, 11.3 mmole). After 1 hour at 25°C. the solution is taken up in a syringe and added slowly to a solution of benzoyl chloride (1.45 g, 10.3 mmole) in ether (30 ml) at −70° C. After 5 minutes aqueous ammonium chloride is added and the products isolated by ether extraction. The residue, after evaporation of the ether, is recrystallized from carbon tetrachloride to afford 2.1 g of the 4-benzoyl compound.

4-Benzoyl-5α-pregnane, 3,20-dione

The acetal (1.1 g) in acetone (100 ml) containing p-toluenesulfonic acid (100 mg) is stirred overnight at 25° C., then the solvent evaporated. The residue is dissolved in ether and washed with aqueous NaHCO$_3$, then dried and evaporated to afford the 4-benzoyl 3,20-dione (800 mg).

4-Diazo-5α-pregnane-3,20-dione

The 4-benzoyl 3,20-dione (355 mg, 0.8 mmole) in tetrahydrofuran (2.0 ml) is added to sodium hydride (48 mg, of a 50% dispersion) in tetrahydrofuran (5ml). After 30 minutes, tosylazide (157 mg, 0.8 mmole) in tetrahydrofuran is added and the mixture stirred overnight at 25° C. Ether is then added, the mixture filtered, then washed with water, dried and evaporated. The residue is chromatographed, the fraction eluted with 70% ether-petrol being collected. Recrystallization from chlorform-hexane affords yellow crystals (40mg) of the desired product.

EXAMPLE 9

Conversion of 4′, 5′-dihydrospiro [androst-4-ene-17,2′(3′H)furan]-3-one to the corresponding 4-diazo compound is represented by the following formula sequence:

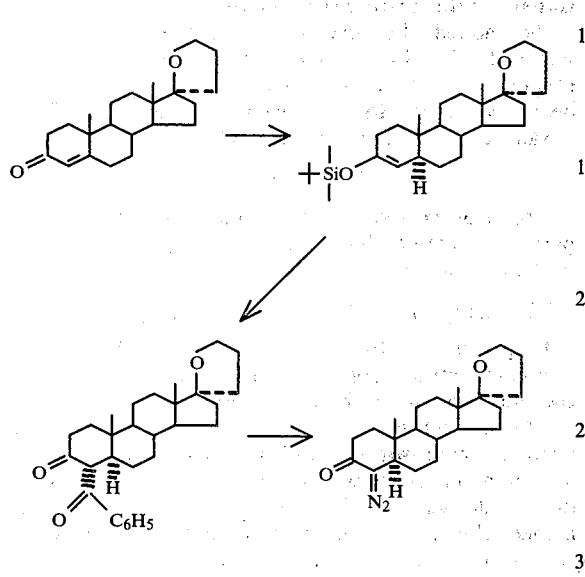

4′,5′-Dihydrospiro[3-trimethylsiloxy-5α-androst-3-ene-17,2′(3′H) furan]

4′,5′-Dihydrospiro[androst-4-ene-17,2′(3′H)furan]-3-one (9.8 g, 30 mmole) in tetrahydrofuran (70 ml) is added to ammonia containing aniline (2.7 g, 30 mmole) and lithium (625 mg, 89 mmole). After 1 hour the blue solution is treated dropwise with isoprene until the blue color dissipates. The ammonia is allowed to evaporate and the residue dried under vacuum (0.5 mm). Tetrahydrofuran (50 ml) is then added, the solution cooled to 0° C., and treated with a solution of trimethylsilyl chloride (12ml) and triethylamine (12ml) which had previously been centrifuged. After 15 minutes the mixture is diluted with pentane and washed with chilled aqueous sodium bicarbonate, then dried (MgSO4) and concentrated. The residue is crystallized from ethyl acetate to afford 7.0 g of the 3-enol ether.

4′,5′-Dihydrospiro[4-benzoyl-5α-androstane-17,2′(3′-H)- furan]-3-one

To the enol ether (4.5 g, 10.27 mmole) in ether (20 ml) is added methyl lithium (5.5 ml of a 2.05 M solution, 11.3 mmole). After 1 hour at 25° C. the solution is taken up in a syringe and added slowly to a solution of benzoyl chloride (1.45 g, 10.3 mmole) in ether (30 ml) at −70° C. After 5 minutes aqueous ammonium chloride is added and the products isolated by ether extraction. The residue, after evaporation of the ether, is recrystallized from carbon tetrachloride to afford 2.2 g of the 4-benzoyl compound.

4′,5′-Dihydro[4-diazo-5α-androstane-17,2′(3′-H) furan]-3-one

The 4-benzoyl compound (320 mg, 0.8 mmole) in tetrahydrofuran (2.0 ml) is added to sodium hydride (48 mg, of a 50% dispersion) in tetrahydrofuran (5ml). After 30 minutes, tosylazide (157 mg, 0.8 mmole) in tetrahydrofuran is added and the mixture stirred overnight at 25° C. Ether is then added, the mixture filtered, then washed with water, dried and evaporated. The residue is chromatographed, the fraction eluted with 70% ether-petrol being collected. Recrystallized from chloroform-hexane affords the desired product as yellow crystals (35 mg).

EXAMPLE 10

Alternatively, the protection-deprotection sequence may be achieved by beginning with an aldehyde, for example, as illustrated in the reactin sequence flow sheet which follows.

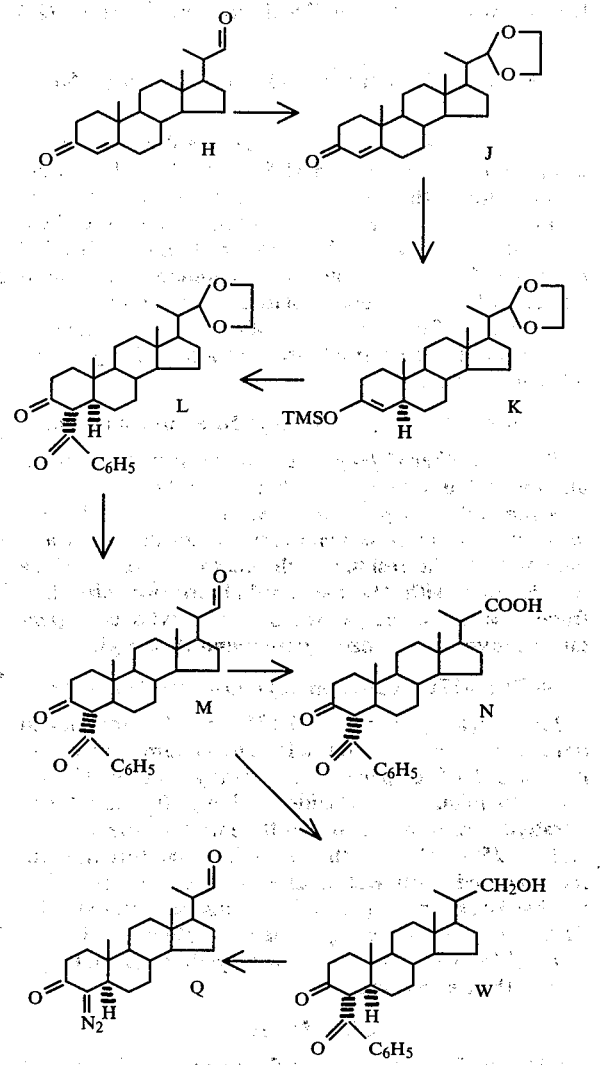

Thus, compound H is protected as an acetal by treatment of 1 equivalent of aldehyde with 1 equivalent of ethyleneglycol using p-toluenesulfonic acid as a catalyst in benzene or toluene solution at a temperature of about 80° to 120° C. and removing excess water, for example, by using a Dean Stark trap. The aldehyde, protected as the acetal, is then subjected to dissolving metal reduction using lithium and ammonia in aniline or tert-butanol at −78° to 33° C. for 1 to 60 minutes. The enolate ion is trapped with trimethylsilyl chloride as described above. The enolate anion is regenerated using alkyl lithiums, e.g., methyl or butyl lithium in ethers, such as, tetrahydrofuran or diethyl ether at 0° to 25° C. for 1 to 60 minutes and is reacted with benzoyl chloride or a lower alkyl acid chloride for 1 to 20 minutes at −100° to −70° C. in, e.g., diethyl ether or tetrahydrofuran to give Compound L.

The aldehyde function is regenerated by treatment with acetone and butanone in the presence of a catalytic amount of p-toluenesulfonic acid or mineral acid for 1 to 24 hours at 25° to 50° C. The aldehyde function can then be converted to the corresponding alcohol by reduction by procedures generally known in the art, e.g., by treatment with borohydride in lower alcohols, e.g., ethanol or tetrahydrofuran at 0° to 25° C. for 1 to 12 hours with subsequentintroduction of the diazo group. The diazo transfer is achieved by using p-toluenesulfonyl azide and, if desired, the alcohol is oxidized to the aldehyde, both by procedures described earlier.

(5α,20R)-4-Diazo-3-oxopregnan-20-carboxaldehyde (Compound Q)

(20R)-21-ethylenedioxy-20-methylpregn-4-en-3-one (Compound J, 2.0 g, 4.5 mmole) in tetrahydrofuran (20 ml) is added to ammonia containing aniline (420 mg, 4.5 mmole) and lithium (100 mg, 15 mmole). After 1 hour the blue solution is treated dropwise with isoprene until the blue color dissipates. The ammonia is allowed to evaporate and the residue dried under vacuum (0.5 mm). Tetrahydrofuran (20 ml) is then added, the solution cooled to 0° C., and treated with a solution of trimethylsilyl chloride (4 ml) and triethylamine (4 ml) which had previously been centrifuged. After 15 minutes the mixture is diluted with pentane and washed with chilled 0.5 M HCl, then chilled aqueous sodium bicarbonate, then dried (MgSO4) and concentrated. The residue is crystallized from ethyl acetate to afford 1.6 g of the enol ether (Compound K).

To the enol ether (5α,20R)-3-trimethylsiloxy-21-ethylenedioxy-20-methylpregn-3-ene (5.08 g, 9.8 mmole) in ether (20 ml) is added methyl lithium (5.5 ml of a 2.05 M solution, 11.3 mmole). After 1 hour at 25° C. the solution is taken up in a syringe and added slowly to a solution of benzoyl chloride (1.54 g, 1.27 mmole) in ether (30 ml) at −70° C. After 5 minutes aqueous ammonium chloride is added and the products isolated by ether extraction. The residue, after evaporation of the ether, is recrystallized from chloroform-heptane to afford 450 mg of the 4-benzoyl acetal (Compound L).

The acetal (1 g) in acetone (200 ml) containing p-toluenesulfonic acid (50 mg) is stirred overnight at 25° C., then concentrated. The residue is crystallized from dichloromethane-heptane to afford the aldehyde (Compound M).

The (5α,20R)-4-benzoyl-3-oxopregnane-20-carboxaldehyde (436 mg, 1.0 mmole) in tetrahydrofuran:methanol (2.0 ml, 1:1) is mixed with sodium borohydride (9.5 mg, 0.25 mmole) at 0° C. for 1 hours. The mixture is then diluted with ether and washed with 0.5 N hydrochloric acid and brine and then dried and the solvent is evaporated to leave, as a resiue, (5α,20R)-4-benzoyl-21-hydroxy-20 -methylpregnan-3-one.

EXAMPLE 11

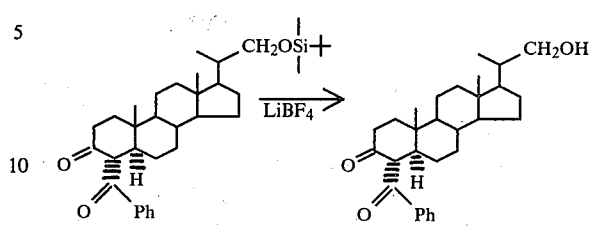

To the silyl ether (5.5 g, 10 mmole) in methylene chloride (200 ml) and acetonitrile (125 ml) is added lithiumtetrafluoroborate (2.8 g, 30 mmole) and the mixture is stirred at room temperature for 60 hours. The mixture is then washed with water, aqueous NaHCO3 and aqueous NaCl then dried (MgSO4) and concentrated. The residue is recrystallized from methylenechloride-heptane to afford the alcohol (3.8 g, 86%).

What is claimed is:

1. A compound of the formula:

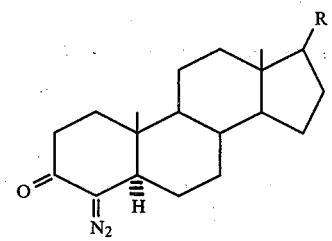

wherein R is:
=O, —OH, —OCO—alkyl $C_{1-5}$, —CH2OH, —CHO, —COCH3,

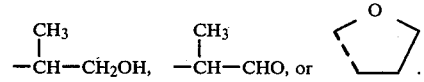

2. A compound of claim 1 wherein R is =O, —OH, —OCO—alkyl $C_{1-5}$, —CH2OH, —CHO, —COCH3,

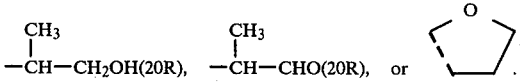

3. A compound of claim 1 wherein R is =O, —OH, —OCO—alkyl $C_{1-5}$, —CH2OH, —CHO, —COCH3,

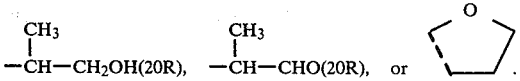

4. A compound of claim 1 wherein R is

5. A compound of claim 1 wherein R is

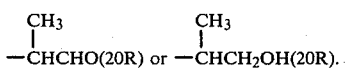

6. A compound of claim 1 which is (5α,20R)-4-diazo-21-hydroxy-20-methylpregnan-3-one.

7. A method of treating acne or oily skin in a patient in need thereof which comprises administering to said patient an effective amount of a compound of claim 1.

8. The method of claim 7 wherein the compound is administered as a topical preparation containing from 0.001% to 5% of the compound.

9. The method of claim 7 wherein the compound is administered as a topical preparation containing from 0.005% to 1% of the compound.

10. The method of claim 7 wherein R is

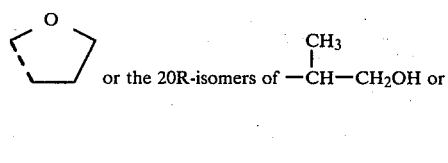

11. The method of claim 7 wherein the compound administered is (5α,20R)-4-diazo-21-hydroxy-20-methyl-pregnan-3-one.

12. A method of treating prostate hypertrophy in a patient in need thereof which comprises administering to said patient an effective amount of a compound of claim 1.

13. The method of claim 12 wherein R is

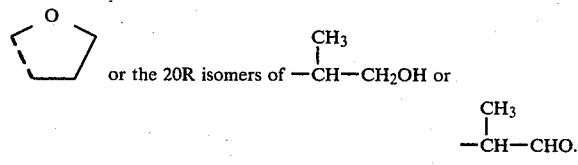

14. The method of claim 12 wherein the compound administered is (5α,20R)-4-diazo-21-hydroxy-20-methyl-pregnan-3-one.

15. A pharmaceutical composition comprising a compound of claim 1 and a pharmaceutically acceptable carrier.

16. A process for preparing a compound of claim 1 which comprises starting with a compound having the formula

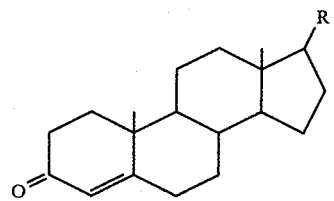

wherein R is as defined in claim 1, being blocked when appropriate forming a siloxy ether or a ketal, subjecting said compound to dissolving metal reduction and reaction with trimethylsilyl chloride forming thereby a compound of the formula

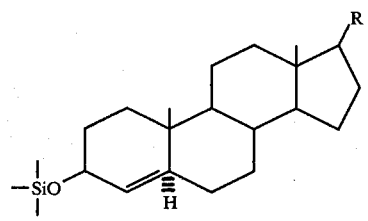

then reacting with an alkyl lithium and with benzoyl chloride or a lower alkyl C$_{1-4}$ acid chloride forming thereby a compound of the formula

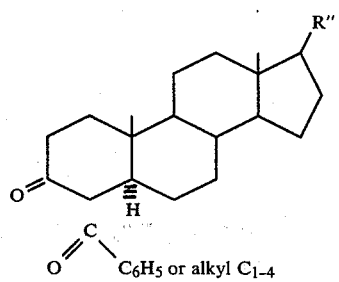

then removing any siloxy ether or ketal blocking groups in R, said siloxy ether being removed by treatment with fluoride ion, acid, or a tetrafluoroborate salt and said ketal being removed by treatment with acetone or butanone in the presence of a catalytic amount of p-toluenesulfonic acid, thereafter reacting with sodium hydride or a lower trialkylamine and p-toluenesulfonyl azide forming thereby a compound of the formula

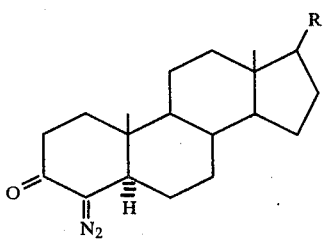

* * * * *

UNITED STATES PATENT AND TRADEMARK OFFICE
CERTIFICATE OF CORRECTION

PATENT NO. : 4,317,817

DATED : March 2, 1982

INVENTOR(S) : Thomas R. Blohm; Brian W. Metcalf

It is certified that error appears in the above-identified patent and that said Letters Patent are hereby corrected as shown below:

Column 2, line 68, "R-configuration" should read -- S-configuration --. Column 4, line 23, in the chemical name, "(5α,20R)" should read -- (5α,20S) --. Column 4, line 35, in the chemical name, "(5α,20R)" should read -- (5α,20S) --. Column 6, line 16, in the chemical name, "(5α,20R)" should read -- (5α,20S) --. Column 6, line 30, in the chemical name, "(5α,20R)" should read -- (5α,20S) --. Column 6, line 48, in the chemical name, "(5α,20R)" should read -- (5α,20S) --. Column 6, line 67, in the chemical name, "(5α,20R)" should read -- (5α,20S) --. Column 7, line 16, in the chemical name, "(5α,20R)" should read -- (5α,20S) --. Column 7, line 25, in the chemical name, "(5α,20R)" should read -- (5α,20S) --. Column 7, line 29, in the chemical name, "(5α,20R)" should read -- (5α,20S) --. Column 7, line 33, in the chemical name, "(5α,20R)" should read -- (5α,20S) --. Column 7, line 39, in the chemical name, "(5α,20R)" should read -- (5α,20S) --. Column 7, line 43, in the chemical name, "(5α,20R)" should read -- (5α,20S) --. Column 7, line 48, in the chemical name, "(5α,20R)" should read -- (5α,20S) --. Column 7, line 67, in the chemical name, "(5α,20R)" should read -- (5α,20S) --. Column 8, line 17, in the chemical name, "(5α,20R)" should read -- (5α,20S) --. Column 9, line 14, in the chemical name, "(5α,20R)" should read -- (5α,20S) --. Column 9, line 29, in the chemical name, "(5α,20R)" should read -- (5α,20S) --. Column 9, line 37, in the chemical name, "(5α,20R)" should read -- (5α,20S) --. Column 9, line 46, in the chemical name, "(5α,20R)" should read -- (5α,20S) --. Column 9, line 66, in the chemical name, "(5α,20R)" should read -- (5α,20S) --. Column 10, line 5, in the chemical name, "(5α,20R)" should read -- (5α,20S) --. Column 10, line 10, in the chemical name, "(5α,20R)" should read -- (5α,20S) --. Column 14, line 55, in the chemical name, "(20R)" should read -- (20S) --. Column 14, line 56, in the chemical name, "(20R)" should read -- (20S) --. Column 15, line 1, in the chemical name, "(20R)" should read -- (20S) --.

UNITED STATES PATENT AND TRADEMARK OFFICE
CERTIFICATE OF CORRECTION

PATENT NO. : 4,317,817

DATED : March 2, 1982

INVENTOR(S) : Thomas R. Blohm; Brian W. Metcalf

It is certified that error appears in the above-identified patent and that said Letters Patent are hereby corrected as shown below:

Column 15, line 4, in the chemical name, "(20R)" should read -- (20S) --. Column 15, line 12, in the chemical name, "(5α,-20R)" should read -- (5α,20S) --. Column 15, line 14, in the chemical name, "(20R)" should read -- (20S) --. Column 15, line 31, in the chemical name, "(5α,20R)" should read -- (5α,20S) --. Column 15, line 33, in the chemical name, "(5α,20R)" should read -- (5α,20S) --. Column 15, line 45, in the chemical name, "(5α,-20R)" should read -- (5α,20S) --. Column 15, line 47, in the chemical name, "(5α,20R)" should read -- (5α,20S) --. Column 15, line 57, in the chemical name, "(5α,20R)" should read -- (5α,-20S) --. Column 15, line 58, in the chemical name, "(5α,20R)" should read -- (5α,20S) --. Column 16, line 1, in the chemical name, "(5α,20R)" should read -- (5α,20S) --. Column 16, line 4, in the chemical name, "(20S)" should read -- (20R) --. Column 16, line 5, in the chemical name, "(20S)" should read -- (20R) --. Column 16, line 8, in the chemical name, "(5α,20R)" should read -- (5α,20S) --. Column 16, line 9, in the chemical name, "(5α,20R)" should read -- (5α,20S) --. Column 16, line 17, in the chemical name, "(5α,20R)" should read -- (5α,20S) --. Column 21, line 22, in the chemical name, "(5α,20R)" should read -- (5α,-20S) --. Column 21, line 24, in the chemical name, "(20R)" should read -- (20S) --. Column 21, line 42, in the chemical name, "(5α,20R)" should read -- (5α,20S) --. Column 21, line 60, in the chemical name, "(5α,20R)" should read -- (5α,20S) --. Column 21, line 67, in the chemical name, "(5α,20R)" should read -- (5α,20S) --. Column 22, line 51 (both appearances), in the chemical structure, "(20R)" should read -- (20S) --. Column 22, line 59 (both appearances), in the chemical structure, "(20R)" should read -- (20S) --. Column 22, line 66 (both appearances), in the chemical structure, "(20R)" should read -- (20S) --.

UNITED STATES PATENT AND TRADEMARK OFFICE
CERTIFICATE OF CORRECTION

PATENT NO. : 4,317,817

DATED : March 2, 1982

INVENTOR(S) : Thomas R. Blohm; Brian W. Metcalf

It is certified that error appears in the above-identified patent and that said Letters Patent are hereby corrected as shown below:

Column 23, line 4 (both appearances), in the chemical structure, "(20R)" should read -- (20S) --.  Column 23, line 7, in the chemical name, "(5α,20R)" should read -- (5α,20S) --.  Column 23, line 26, "20R-isomers" should read -- 20S-isomers --.  Column 23, line 34, in the chemical name, "(5α,20R)" should read -- (5α,-20S) --.  Column 23, line 46, "20R-isomers" should read -- 20S-isomers --.  Column 23, line 52, in the chemical name, "(5α,20R)" should read -- (5α,20S) --.

Signed and Sealed this

First Day of July 1986

[SEAL]

Attest:

DONALD J. QUIGG

Attesting Officer

Commissioner of Patents and Trademarks